United States Patent [19]

Gayer et al.

[11] Patent Number: 5,420,160
[45] Date of Patent: May 30, 1995

[54] 1-ALKOXYHEXATRIENE-2-CARBOXYLATES

[75] Inventors: Herbert Gayer, Monheim-Baumberg; Peter Gerdes, Aachen; Heinz-Wilhelm Dehne, Monheim; Stefan Dutzmann, Hilden, all of Germany

[73] Assignee: Bayer Aktiengesellschaft, Leverkusen, Germany

[21] Appl. No.: 184,732

[22] Filed: Jan. 21, 1994

Related U.S. Application Data

[63] Continuation of Ser. No. 939,176, Sep. 2, 1992, abandoned.

[30] Foreign Application Priority Data

Sep. 10, 1991 [DE] Germany ............... 41 29 962.0

[51] Int. Cl.$^6$ ............... A01N 27/00; A01N 29/04; A01N 31/08; A01N 33/18
[52] U.S. Cl. ............... 514/532; 514/534; 514/535; 514/538; 514/545; 514/689; 514/709; 514/710; 560/11; 560/20; 560/21; 560/23; 560/37; 560/45; 560/53; 560/60; 560/104; 560/105
[58] Field of Search ............... 560/60, 11, 20, 21, 560/23, 37, 45, 53, 104, 105; 514/532, 534, 535, 538, 545, 689, 709, 710

[56] References Cited

U.S. PATENT DOCUMENTS 4,334,696 6/1982 Steglich et al.

OTHER PUBLICATIONS

Weber et al., "Strobilurin D and Strobilurin F: Two New Cytastatic and Antifungal (E)-β-Methoxyacrylate Antibiotics from Cyphellopsis anomala (1)", Oct. 1990, *Planta Medica, Journal of Medicinal Plant Research*, vol. 56(5), pp. 446-450.

Fredenhagen et al., "Strobilurins F, G and H, Three New Antifungal Metabolites From Bolinea Lutea", Jun. 1990, *The Journal of Antibiotics*, vol. 43(6), pp. 661-667.

Tetrahedron Lett., Bd. 30, Nr. 40, 1989, Seiten 5417-5420, Sutter, M., "First Total Synthesis of Strobilurin B".

J. Antibiot., Bd., 43, Nr. 6, 1990, Seiten 655-660, Fredenhagen et al., "Strobilurins F, G and H, Three New Antifungal Metabolites from Bolinea Lutea".

Anke et al, "Synthese von Strobilurin A and Revision der Stereochemie":, Liebigs Ann. Chem. (1984) pp. 1616-1625.

Schramm et al, "Strobilurin A and B, antifungische Stoffwechselprodukte . . . ", Chem. Ber. V. 111 (1978) pp. 1779-1784.

Nerud et al, "Biosynthesis of Mucidin, an antifungal antibiotic . . . ", Collect. Czech. Chem. Commun. V. 47 (1982), pp. 1020-1025.

Vondracek et al, "Another Antibiotic from the Basidiomycete", Connect. Czech. Chem. Commun., vol. 48, (1983) pp. 1508-1512.

*Primary Examiner*—José G. Dees
*Assistant Examiner*—Dwayne C. Jones
*Attorney, Agent, or Firm*—Sprung, Horn, Kramer & Woods

[57] ABSTRACT

There are described new 1-alkoxyhexatriene-2-carboxylates of the formula (I)

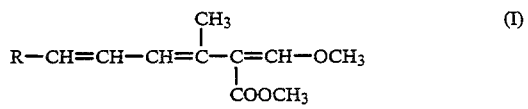

in which

R represents substituted phenyl, and a plurality of processes for their preparation.

The new 1-alkoxyhexytriene-2-carboxylates are used as pesticides.

3 Claims, No Drawings

1-ALKOXYHEXATRIENE-2-CARBOXYLATES

This application is a continuation of application Ser. No. 939,176, filed Sep. 2, 1992, now abandoned.

The invention relates to new 1-alkoxyhexatriene-2-carboxylates, to a plurality of processes for their preparation, and to their use as pesticides.

It is known that certain 1-alkoxyhexatriene-2-carboxylates such as, for example, the compound methyl 1-methoxy-3-methyl-6-phenyl-hexatriene-2-carboxylate or the compound methyl 1-methoxy-3-methyl-6-(4-methoxyphenyl)-hexatriene-2-carboxylate, have fungicidal properties (compare, for example, Chem. Ber. 111, 2779–2784 [1978]; Liebigs Ann. Chem., 1984, 1616–25; DE 3,025,368; Collect. Czech. Chem. Commun., 47, 1020–1025 [1982]; Collect. Czech. Chem. Commun., 48, 1508–1512 [1983]).

However, the activity of these previously known compounds is not entirely satisfactory in all fields of application, in particular when low amounts and concentrations are applied.

There have been found new 1-alkoxyhexatriene-2-carboxylates of the general formula (I)

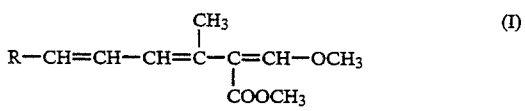

in which
R represents substituted phenyl, suitable substituents being: halogen, cyano, nitro, alkyl, alkenyl, alkinyl, alkoxy, alkenyloxy, alkinyloxy, alkylthio, alkylsulphinyl, alkylsulphonyl, halogenoalkyl, halogenoalkenyl, halogenoalkinyl, halogenoalkoxy, halogenoalkenyloxy, halogenoalkinyloxy, halogenoalkylthio, halogenoalkylsulphinyl, halogenoalkylsulphonyl, alkoxycarbonyl, alkoxycarbonylalkyl, alkoximinoalkyl and in each case optionally substituted aralkyl, aralkyloxy, aryl or aryloxy, with the exception of the compounds methyl 1-methoxy-3-methyl-6-(4-methoxyphenyl)-hexatriene-2-carboxylate, methyl 1-methoxy-3-methyl-6-(3-methoxyphenyl)-hexatriene-2-carboxylate, methyl 1-methoxy-3-methyl-6-(4-chloro-3-methoxyphenyl)-hexatriene-2-carboxylate, methyl 1-methoxy-3-methyl-6-[2-(3-methyl-but-2-en-1-yl-oxy)-phenyl]-hexatriene-2-carboxylate and methyl 1-methoxy-3-methyl-6-[3-(3-methyl-but-2-en-1-yl-oxy)-phenyl]-hexatriene-2-carboxylate.

The compounds of the formula (I) can exist in the form of geometric isomers or isomer mixtures of various compositions. The invention claims the pure isomers as well as the isomer mixtures.

Furthermore, it has been found that the new 1-alkoxyhexatriene-2-carboxylates of the general formula (I)

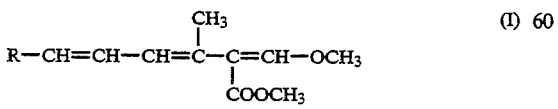

in which
R has the abovementioned meaning
are obtained when methoxymethylenecarboxylates of the formula (II)

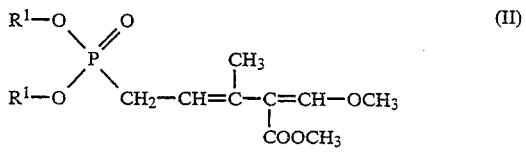

in which
$R^1$ represents alkyl
are reacted with benzaldehydes of the formula (III)

in which
R has the abovementioned meaning,
if appropriate in the presence of a diluent and if appropriate in the presence of a reaction auxiliary.

Finally, it has been found that the 1-alkoxyhexatriene-2-carboxylates of the general formula (I) according to the invention have a good activity against phytopathogenic microorganisms.

Surprisingly, the 1-alkoxyhexatriene-2-carboxylates of the general formula (I) according to the invention have a considerably better fungicidal activity compared with the 1-alkoxyhexatriene-2-carboxylates which are known from the prior art such as, for example, the compound methyl 1-methoxy-3-methyl-6-phenyl-hexatriene-2-carboxylate or the compound methyl 1-methoxy-3-methyl-6-(4-methoxyphenyl)-hexatriene-2-carboxylate, which are similar compounds chemically and from the point of view of their action.

Formula (I) provides a general definition of the 1-alkoxyhexatriene-2-carboxylates according to the invention. Preferred compounds of the formula (I) are those in which R represents phenyl which is optionally monosubstituted or polysubstituted by identical or different substituents, suitable substituents being: halogen, cyano, nitro, in each case straight-chain or branched alkyl, alkoxy or alkylthio, each of which has 1 to 8 carbon atoms, in each case straight-chain or branched alkenyl, alkinyl, alkenyloxy or alkinyloxy, each of which has 2 to 8 carbon atoms, in each case straight-chain or branched halogenoalkyl, halogenoalkoxy or halogenoalkylthio, each of which has 1 to 6 carbon atoms and 1 to 13 identical or different halogen atoms, in each case straight-chain or branched halogenoalkenyl, halogenoalkinyl, halogenoalkenyloxy or halogenoalkinyloxy, each of which has 2 to 6 carbon atoms and 1 to 11 identical or different halogen atoms, in each case straight-chain or branched alkoxycarbonyl, alkoxycarbonylalkyl or alkoximinoalkyl, each of which has 1 to 6 carbon atoms in the individual alkyl moieties, and benzyl, benzyloxy, phenyl or phenoxy, each of which is optionally monosubstituted or polysubstituted by identical or different substituents from the series comprising halogen and/or in each case straight-chain or branched alkyl and/or alkoxy, each of which has 1 to 6 carbon atoms, with the exception of the compounds methyl 1-methoxy-3-methyl-6-(4-methoxyphenyl)-hexatriene-2-carboxylate, methyl 1-methoxy-3-methyl-6-(3-methoxyphenyl)-hexatriene-2-carboxylate, methyl 1-methoxy-3-methyl-6-(4-chloro-3-methoxyphenyl)-hexatriene-2-carboxylate, methyl 1-methoxy-3-methyl-6-[2-(3-methyl-but-2-en-1-yl-oxy)-phenyl]-hexatriene-2-carboxylate and methyl 1-methoxy-3-methyl-6-[3-(3-methyl-but-2-en-1-yl-oxy)-phenyl]-hexatriene-2-carboxylate.

Particularly preferred compounds of the formula (I) are those in which

R represents phenyl which is optionally monosubstituted to pentasubstituted by identical or different substituents, suitable substituents being: halogen, cyano, nitro, in each-case straight-chain or branched alkyl, alkoxy or alkylthio, each of which has 1 to 6 carbon atoms, in each case straight-chain or branched alkenyl, alkinyl, alkenyloxy or alkinyloxy, each of which has 2 to 6 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched halogenoalkenyl, halogenoalkinyl, halogenoalkenyloxy or halogenoalkinyloxy, each of which has 2 to 4 carbon atoms and 1 to 7 identical or different halogen atoms, in each case straight-chain or branched alkoxycarbonyl, alkoxycarbonylalkyl or alkoximinoalkyl, each of which has 1 to 4 carbon atoms in the individual alkyl moieties, and benzyl, benzyloxy, phenyl or phenyloxy, each of which is optionally monosubstituted to trisubstituted by identical or different substituents from the series comprising halogen and/or in each case straight-chain or branched alkyl and-/or alkoxy, each of which has 1 to 4 carbon atoms, with the exception of the compounds methyl 1-methoxy-3-methyl-6-(4-methoxyphenyl)-hexatriene-2-carboxylate, methyl 1-methoxy-3-methyl-6-(3-methoxyphenyl)-hexatriene-2-carboxylate, methyl 1-methoxy-3-methyl-6-(4-chloro-3-methoxyphenyl)-hexatriene-2-carboxylate, methyl 1-methoxy-3-methyl-6-[2-(3-methyl-but-2-en-1-yl-oxy)-phenyl]-hexatriene-2-carboxylate and methyl 1-methoxy-3-methyl-6-[3-(3-methyl-but-2-en-1-yl-oxy)-phenyl]-hexatriene-2-carboxylate.

Very particularly preferred compounds of the formula (I) are those in which

R represents phenyl which is optionally monosubstituted to trisubstituted by identical or different substituents, suitable substituents being fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, in each case straight-chain or branched alkenyl, alkinyl, alkenyloxy or alkinyloxy, each of which has 2 to 4 carbon atoms, in each case straight-chain or branched halogenoalkyl, halogenoalkoxy or halogenoalkylthio, each of which has 1 to 3 carbon atoms and 1 to 7 identical or different halogen atoms, in each case straight-chain or branched halogenoalkenyl, halogenoalkinyl, halogenoalkenyloxy or halogenoalkinyloxy, each of which has 2 to 4 carbon atoms and 1 to 5 identical or different halogen atoms, in each case straight-chain or branched alkoxycarbonyl, alkoxycarbonylalkyl or alkoximinoalkyl, each of which has 1 to 3 carbon atoms in the individual alkyl moieties, and benzyl, benzyloxy, phenyl or phenoxy, each of which is optionally monosubstituted or disubstituted by identical or different substituents from the series comprising fluorine, chlorine, bromine, methyl, ethyl, n- or i-propyl, n-, i-, s- or t-butyl, methoxy, ethoxy, n- or i-propoxy and n-, i-, s- or t-butoxy, with the exception of the compounds methyl 1-methoxy-3-methyl-6-(4-methoxyphenyl)-hexatriene-2-carboxylate, methyl 1-methoxy-3-methyl-6-(3-methoxyphenyl)-hexatriene-2-carboxylate, methyl 1-methoxy-3-methyl-6-(4-chloro-3-methoxyphenyl)-hexatriene-2-carboxylate, methyl 1-methoxy-3-methyl-6-[2-(3-methyl-but-2-en-1-yl-oxy)-phenyl]-hexatriene-2-carboxylate and methyl 1-methoxy-3-methyl-6-[3-(3-methyl-but-2-en-1-yl-oxy)-phenyl]-hexatriene-2-carboxylate.

If, for example, methyl 5-(diethoxyphosphinyl)-1-methoxy-3-methyl-1,3-pentadiene-2-carboxylate and 4-chlorobenzaldehyde are used as starting substances, the course of the reaction of the process according to the invention can be outlined by the following equation:

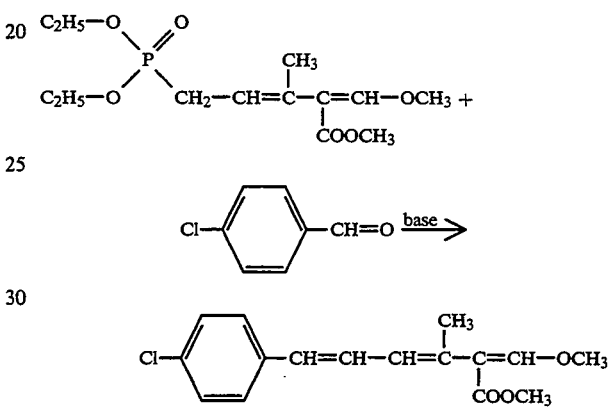

Formula (II) provides a general definition of the methoxymethylenecarboxylates required as starting substances for carrying out the process according to the invention. In this formula (II), $R^1$ preferably represents straight-chain or branched alkyl having 1 to 6, in particular 1 to 3, carbon atoms.

The methoxymethylenecarboxylates of the formula (II) are known (compare, for example, DE 4,012,792).

Formula (III) provides a general definition of the benzaldehydes furthermore required as starting substances for carrying out the process according to the invention. In this formula (III), R preferably represents those radicals which have already been mentioned in connection with the description of the compounds of the formula (I) according to the invention as being preferred for this substituent.

The benzaldehydes of the formula (III) are generally known compounds of organic chemistry.

Suitable diluents for carrying out the process according to the invention are inert organic solvents. These include, in particular, aliphatic, alicyclic or aromatic hydrocarbons such as, for example, benzine, benzene, toluene, xylene, petroleum ether, hexane, cyclohexane; ethers such as diethyl ether, diisopropyl ether, dioxane, tetrahydrofuran or ethylene glycol dimethyl ether or ethylene glycol diethyl ether; amides such as N,N-dimethylformamide, N,N-dimethylacetamide, N-methylformanilide, N-methylpyrrolidone or hexamethylphosphoric triamide, or sulphoxide such as dimethyl sulphoxide.

The process according to the invention is preferably carried out in the presence of a suitable reaction auxiliary. Reaction auxiliaries which are suitable are all customary inorganic and organic bases. These include, for example, the hydrides, hydroxides, amides, alcoholates, acetates, carbonates or hydrogen carbonates of alkaline earth metals or alkali metals, such as, for example, sodium hydride, sodium amide, sodium methylate, sodium ethylate, potassium t-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate.

When carrying out process (a) according to the invention, the reaction temperatures can be varied within a substantial range. In general, the process is carried out at temperatures between −70° C. and 100° C., preferably at temperatures between −30° C. and 50° C.

To carry out the process according to the invention, 1.0 to 1.5 moles, preferably 1.0 to 1.2 moles, of benzaldehyde of the formula (III) and if appropriate 1.0 to 3.0 moles, preferably 1.0 to 1.5 moles, of base used as reaction auxiliary are generally employed per mole of methoxymethylenecarboxylate of the formula (II). The reaction is carried out and the reaction products are worked up and isolated by known processes (compare, in this context, for example DE 4,012,792; J. Amer. Chem. Soc. 83, 1734 [1961] or the Preparation Examples).

The 1-alkoxyhexatriene-2-carboxylates of the formula (I) which can be obtained in this manner are generally mixtures of compounds which are stereoisomers with regard to the three double bonds, with the E,E,E-isomers generally being predominant (compare, in this context, also DE 4,012,792). They can be converted into the E,Z,E-isomers by the use of UV irradiation or by the action of reagents which isomerize double bonds such as, for example iodine in a suitable solvent, such as toluene, these E,Z,E-isomers being identical to the natural substance strobilurin with regard to their stereochemistry (compare, for example, Liebigs Ann. Chem. 9, 1616 [1984] or DE 3,025,368).

The active compounds according to the invention have a powerful action against pests and can be employed in practice for combating undesired harmful organisms. The active compounds are suitable for use as plant protection agents, in particular as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Heiminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilago avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

In this context, the active compounds according to the invention can be employed with particularly good success for combating cereal diseases such as, for example, against the causative organism of net blotch of barley (*Pyrenophora teres*) or against the causative organism of leaf spot of barley (*Cochliobolus sativus*) or against the causative organism of glume blotch of wheat (*Septoria nodorum*) or against the causative organism of powdery mildew of cereals (*Erysiphe graminis*), or for combating diseases in fruit and vegetable growing such as, for example, against the causative organism of tomato blight (*Phytophthora infestans*) or against the causative organism of apple scab (*Venturia inaequalis*), or for combating rice diseases such as, for example, against the causative organism of rice blast disease (*Pyricularia olyzae*). In this context, the active compounds according to the invention also have curative properties as well as protective properties. Moreover, the active compounds according to the invention have a broad in-vitro activity.

Depending on their particular physical and/or chemical properties, the active compounds can be converted into the customary formulations, such as solutions, emulsions, suspensions, powders, foams, pastes, granules, aerosols, very fine capsules in polymeric substances and in coating compositions for seed, as well as ULV cold- and warm-mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilisers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomising, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

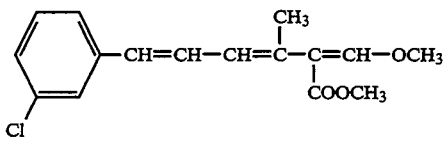

To a mixture of 5.6 g (0.04 mol) of 3-chlorobenzaldehyde and 12.2 g (0.04 mol) of methyl 5-(diethoxyphosphinyl)-1-methoxy-3-methyl-1,3-pentadiene-2-carboxylate in 40 ml of tetrahydrofuran there are added dropwise at −20° C. with stirring 4.5 g (0.04 mol) of potassium tert-butylate in 40 ml of tetrahydrofuran, then, when the addition has ended, the reaction mixture is allowed to come to room temperature and diluted with diethyl ether, washed with water and dried over sodium sulphate, and the solvent is removed in vacuo. The residue is purified by silica gel chromatography (mobile phase: diethyl ether/petroleum ether 1:1).

This gives 6.3 g (54% of theory) of methyl 1-methoxy-3-methyl-6-(3-chlorophenyl)-hexatriene-2-carboxylate which, according to GC/MS analysis, is composed of the following isomers:

E,E,E(43.6%)
 m/e=292,245,233,201,165,155,115,91,75,47,26
E,Z,Z(10.8%)
 m/e=292,245,233,201,165,155,115,91,75,47,26
E,Z,E(21.1%)
 m/e=292,245,233,201,165,155,115,91,75,47,26
Z,E,E(11.9%)
 m/e=292,245,233,201,165,155,115,91,75,47,26

Isomerisation of the stereoisomer mixture:

16 g (0.055 mol) of this mixture in 160 ml of toluene are refluxed with 0.5 g of iodine for 8 hours, a further 0.5 g of iodine is added, and the mixture is refluxed for a further 8 hours. For working up, the reaction mixture is chromatographed on silica gel (mobile phase: diethyl ether/petroleum ether 1:1).

This gives 16 g of crude mixture, 5.9% of which exist in the form of the E,E,E-isomer and 28.2% in the form of the E,Z,E-isomer. Silica gel chromatography (mobile phase: diethyl ether/petroleum ether 1:1) allows the pure E,Z,E-isomer to be isolated.

$^1$H NMR (CDCl$_3$/tetramethylsilane): δ=1.98 (3H); 3.74 (3H); 3.86 (3H); 6.269, 6.273 d (1H); 6.44, 6.56 d (1H); 6.6–6.65 dd (1H); 7.44 (1H); 7.12–7.34 (m (4H) ppm.

The following 1-alkoxyhexatriene-2-carboxylates of the general formula (I)

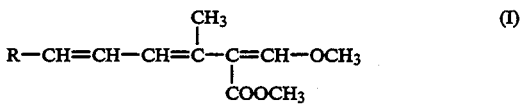

are obtained in a corresponding manner and following the general preparation instructions:

| Ex. No. | R | Mass spectrum [m/e] |
|---|---|---|
| 2 | 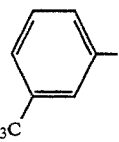 H₃C— (meta) | 272; 240; 225; 213; 181; 135; 115; 105; 75; 47; (26) |
| 3 | 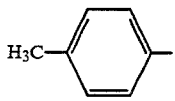 H₃C— (para) | 272; 240; 225; 213; 181; 135; 115; 105; 75; 47 |
| 4 | 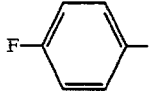 F— (para) | 276; 245; 217; 202; 185; 139; 133; 83; 75; 47 |
| 5 | 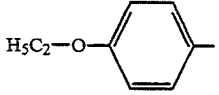 H₅C₂—O— (para) | 302; 271; 243; 227; 211; 165; 137; 128; 91; 75; 47 [¹H NMR*): 2.0; 3.72; 3.84; 6.14; 6.18; 6.46; 6.51; 6.75–7.05; 7.36; 6.8–7.4] |
| 6 | 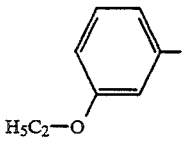 H₅C₂—O— (meta) | 302; 270; 243; 227; 211; 165; 143; 128; 91; 75; 47 |
| 7 | 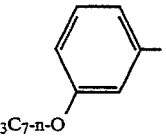 H₃C₇-n-O— | 316; 284; 257; 225; 200; 179; 158; 128; 91; 75; 43 |
| 8 | 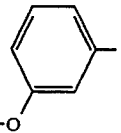 CH₂=CH—CH₂—O— | 314; 283; 241; 223; 198; 177; 141; 128; 91; 75; 41 |
| 9 | 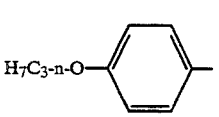 H₇C₃-n-O— (para) | 316; 269; 257; 225; 200; 179; 137; 107; 91; 75; 41 [¹H NMR*): 2.0; 3.72; 3.84; 6.14; 6.17; 6.46; 6.51; 6.7–7.0; 7.35; 6.8–7.31] |
| 10 | 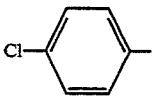 Cl— (para) | 292; 245; 233; 201; 165; 155; 115; 91; 75; 47; 26 |
| 11 | 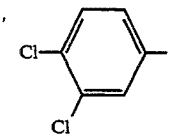 Cl—, Cl (dichloro) | 326; 295; 267; 252; 235; 189; 165; 152; 126; 87 |
| 12 | 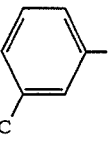 F₃C— | 326; 307; 267; 252; 235; 189; 183; 159; 115; 91 |

*)¹H NMR spectra in deuterochloroform (CDCl₃) with tetramethylsilane (TMS) as the internal standard. The data given are the chemical shift as δ value in ppm.

Use Examples

In the Use Examples which follow, the compounds listed below are employed as comparison substances:

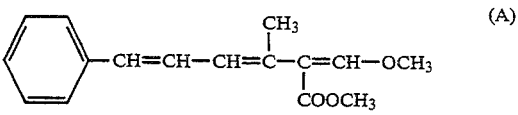

(A)

Methyl 1-methoxy-3-methyl-6-phenyl-hexatriene-2-carboxylate

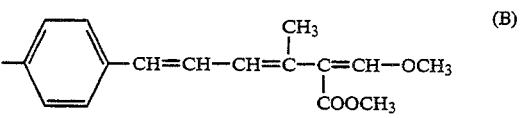

(B)

Methyl 1-methoxy-3-methyl-6-(4-methoxyphenyl)-hexatriene-2-carboxylate

Example A

Venturia test (apple)/protective
Solvent: 4.7 parts by weight of acetone
Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in the greenhouse at 20° C. and a relative atmospheric humidity of approx. 70%.

The test is evaluated 12 days after inoculation.

An activity which exceeds the prior art by more than 100% is shown, in this test, for example by the compounds of the following Preparation Examples: 1, 2, 3, 5, 10 and 11 at an active compound concentration of 10 ppm.

Example B

Phytophthora test (tomato)/curative
Solvent: 4.7 parts by weight of acetone
Emulsifier: 0.3 parts by weight of alky-aryl polyglycol ether To produce a suitable preparation of active compound, 1 part by weight of active compound is mixed with the stated amounts of solvent and emulsifier, and the concentrate is diluted with water to the desired concentration.

To test for curative activity, young plants are inoculated with an aqueous spore suspension of Phytophthora infestans. The plants remain in an incubation cabin at 20° C. and 100% relative atmospheric humidity for 7 hours. After a short drying-off time, the plants are sprayed with the preparation of active compound until dripping wet.

The plants are then placed in an incubation cabin at 20° C. and a relative atmospheric humidity of approx. 100%.

The test is evaluated 3 days after inoculation.

An activity which exceeds the prior art by up to 90% is shown, in this test, for example by the compounds of the following Preparation Examples: 4, 5, 7, 9 and 10 at an active compound concentration of 50 ppm.

Example C

*Cochliobolus sativus* test (barley)/protective

Solvent: 100 parts by weight of dimethylformamide
Emulsifier: 0.25 parts by weight of alkyl-aryl polyglycol ether To product a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Cochliobolus sativus. The plants remain in an incubation cabin at 20° C. and 100% relative atmospheric humidity for 48 hours.

The plants are then placed in an incubation cabin at 20° C. and a relative atmospheric humidity of approx. 80%.

The test is evaluated 7 days after inoculation.

An activity which exceeds the prior art by more than 100% is shown, in this test, for example by the compounds of the following Preparation Examples: 2 and 4 at an active compound concentration of 100 ppm.

Example D

Pyrenophora teres test (barley)/protective

Solvent: 100 parts by weight of dimethylformamide
Emulsifier: 0.25 parts by weight of alkyl-aryl polyglycol ether To product a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Pyrenophora teres. The plants remain in an incubation cabin at 20° C. and 100% relative atmospheric humidity for 48 hours.

The plants are then placed in a greenhouse at 20° C. and a relative atmospheric humidity of approx. 80%.

The test is evaluated 7 days after inoculation.

An activity which exceeds the prior art by more than 100% is shown, in this test, for example by the compound of Preparation Example 2 at an active compound concentration of 100 ppm.

We claim:

1. 1-Alkoxyhexatriene-2-carboxylates of the formula:

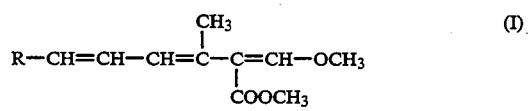

in which

R represents substituted phenyl, wherein substituents are selected from the group consisting of halogen, cyano, nitro, alkyl, alkenyl, alkynyl, alkynyloxy, alkylthio, alkylsulphinyl, alkylsulphonyl, halogenoalkyl, halogenoalkenyl, halogenoalkynyl, halogenoalkoxy, halogenoalkenyloxy, halogenoalkynyloxy, halogenoalkylthio, halogenoalkylsulphinyl, halogenoalkylsulphonyl, alkoxycarbonyl, alkoxycarbonylalkyl, alkoximinoalkyl, and aralkyl, aralkyloxy, aryl or aryloxy, each of which is optionally substituted by halogen, straight-chain or branched $C_{1-6}$-alkyl or straight-chain or branched $C_{1-6}$-alkoxy.

2. A pesticidal composition comprising a pesticidally effective amount of at least one 1-alkoxyhexatriene-2-carboxylate of the formula (I) according to claim 1 and an extender.

3. A method of combating pests comprising applying to said pests or their habitat a pesticidally effective amount of at least one 1-alkoxyhexatriene-2-carboxylate of the formula (I) according to claim 1.

* * * * *